017
United States Patent [19]

Banks et al.

[11] 4,071,471

[45] Jan. 31, 1978

[54] CATALYSTS FOR CONVERSION OF OLEFINS

[75] Inventors: Robert L. Banks; Joseph R. Kenton, both of Bartlesville, Okla.

[73] Assignee: Phillips Petroleum Company, Bartlesville, Okla.

[21] Appl. No.: 711,027

[22] Filed: Aug. 2, 1976

Related U.S. Application Data

[60] Division of Ser. No. 535,299, Dec. 23, 1974, Pat. No. 3,996,166, which is a division of Ser. No. 205,350, Dec. 6, 1971, Pat. No. 3,865,751, which is a division of Ser. No. 6,045, Jan. 26, 1970, Pat. No. 3,660,506, which is a continuation of Ser. No. 678,499, Oct. 27, 1967, abandoned, which is a continuation-in-part of Ser. No. 627,668, April 3, 1967, abandoned.

[51] Int. Cl.² .................... B01J 27/24; B01J 27/02
[52] U.S. Cl. .................... 252/437; 252/439; 252/457; 252/475
[58] Field of Search ............... 252/437, 439, 465, 475

[56] References Cited

U.S. PATENT DOCUMENTS

| 3,707,581 | 12/1972 | Heckelsberg | 260/683 D |
|---|---|---|---|
| 3,865,751 | 2/1975 | Banks et al. | 252/457 |
| 3,915,897 | 10/1975 | Reusser et al. | 252/457 |
| 3,996,166 | 12/1976 | Banks et al. | 252/437 |

*Primary Examiner*—Carl F. Dees

[57] ABSTRACT

A composition active for the conversion of olefins comprising magnesium oxide and an olefin disproportionation catalyst in admixture.

8 Claims, No Drawings

CATALYSTS FOR CONVERSION OF OLEFINS

This application is a division of application Ser. No. 535,299, filed Dec. 23, 1974, now U.S. Pat. No. 3,996,166 which in turn was a division of application Ser. No. 205,350, filed Dec. 6, 1971, now U.S. Pat. No. 3,865,751, which in turn was a division of application Ser. No. 6,045, filed Jan. 26, 1970, now U.S. Pat. No. 3,660,506, which in turn was a continuation of application Ser. No. 678,499, filed Oct. 27, 1967, now abandoned, which in turn was a continuation-in-part of application Ser. No. 627,668, filed Apr. 3, 1967, now abandoned.

This invention relates to the conversion of olefin hydrocarbons by the olefin reaction.

The olefin reaction is defined as a process for the catalytic conversion over a catalyst of a feed comprising one or more ethylenically unsaturated compounds to produce a resulting product which contains at least ten percent by weight of product compounds, which product compounds can be visualized as resulting from at least one primary reaction, as defined below, or the combination of at least one primary reaction and at least one unsaturated bond isomerization reaction, and wherein the sum of the compounds contained in said resulting product consisting of hydrogen, saturated hydrocarbons, and compounds which can be visualized as formed by skeletal isomerization but which cannot be visualized as formed by one or more of the above-noted reactions, comprises less than 25 percent by weight of the total of said resulting product. Feed components and unsaturated bond isomers thereof are not included in the resulting product for the purpose of determining the above-noted percentages.

In the olefin reaction, as defined above, the primary reaction is a reaction which can be visualized as comprising the breaking of two existing unsaturated bonds between first and second carbon atoms and between third and fourth carbon atoms, respectively, and the formation of two new unsaturated bonds between said first and third and between said second and fourth carbon atoms. Said first and second carbon atoms and said third and fourth carbon atoms can be in the same or different molecules.

The olefin reaction according to this invention is illustrated by the following reactions:

1. The disproportionation of an acyclic mono- or polyene having at least three carbon atoms into other acyclic mono- or polyenes of both higher and lower number of carbon atoms; for example, the disproportionation of propylene yields ethylene and butenes; the disproportionation of 1,5-hexadiene yields ethylene and 1,5,9-decatriene;

2. The conversion of an acyclic mono- or polyene having three or more carbon atoms and a different acyclic mono- or polyene having three or more carbon atoms to produce different acyclic olefins; for example, the conversion of propylene and iosbutylene yields ethylene and isopentene;

3. The conversion of ethylene and an internal acyclic mono- or polyene having four or more carbon atoms to produce other olefins having a lower number of carbon atoms than that of the acyclic mono- or polyenes; for example, the conversion of ethylene and 4-methylpentene-2 yields 3-methylbutene-1 and propylene;

4. The conversion of ethylene or an acyclic mono- or polyene having three or more carbon atoms and a cyclic mono- or cyclic polyene to produce an acyclic polyene having a higher number of carbon atoms than that of any of the starting materials; for example, the conversion of cyclohexene and 2-butene yields 2,8-decadiene; the conversion of 1,5-cyclooctadiene and ethylene yields 1,5,9-decatriene;

5. The conversion of one or more cyclic mono- or cyclic polyenes to produce a cyclic polyene having a number of carbon atoms than any of the starting materials; for example, the conversion of cyclopentene yields 1,6-cyclodecadiene and continued reaction can produce higher molecular weight material.

6. The conversion of an acyclic polyene having at least seven carbon atoms and having at least five carbon atoms between any two double bonds to produce acyclic and cyclic mono- and polyenes having a lower number of carbon atoms than that of the feed; for example, the conversion of 1,7-octadiene yields cyclohexene and ethylene; or 7. The conversion of one or more acyclic polyenes having at least three carbon atoms between any two double bonds to produce acyclic and cyclic mono- and polyenes generally having both a higher and lower number of carbon atoms than that of the feed material; for example, the conversion of 1,4-pentadiene yields 1,4-cyclohexadiene and ethylene.

By disproportionation as used herein is meant the conversion of hydrocarbons into similar hydrocarbons of both higher and lower numbers of carbon atoms.

An object of this invention is to convert olefins by the olefin reaction.

Another object of this invention is to disproportionate olefins at relatively high conversion rates.

Other aspects, objects and the advantages of our invention are apparent in the written description and the claims.

According to this invention, an olefin capable of undergoing the olefin reaction is converted by contacting with a combined catalyst comprising an olefin reaction catalyst and a double bond isomerization catalyst under suitable conditions for obtaining olefin reaction. Further according to the invention an olefin capable of undergoing the olefin reaction is converted by contacting with a mixed bed of a disproportionation catalyst and magnesium oxide. Further according to the invention an olefin capable of undergoing the olefin reaction is converted by contacting with a disproportionation catalyst treated with a metallic alkali metal.

Olefins applicable for use in the process of the invention include acyclic mono- and polyenes having at least 3 carbon atoms per molecule and cycloalkyl and aryl derivatives thereof; cyclic mono- and polyenes having at least four carbon atoms per molecule and alkyl and aryl derivatives thereof; mixtures of two or more of the above olefins; and mixtures of ethylene with one or more of the above olefins. Many useful reactions are accomplished with such acyclic olefins having 3–30 carbon atoms per molecule and with such cyclic olefins having 4–30 carbon atoms per molecule.

Some specific examples of acyclic olefins suitable for reactions of this invention include propylene, 1-butene, isobutene, 2-butene, 1,3-butadiene, 1-pentene, 2-pentene, isoprene, 1-hexene, 1,4-hexadiene, 2-heptene, 1-octene, 2,5-octadiene, 2,4,6-octatriene, 2-nonene, 1-dodecene, 2-tetradecene, 1-hexadecene, 5,6-dimethyl-2,4-octadiene, 2-methyl-1butene, 2-methyl-2-butene, 1,3-dodecadiene, 1,3,6-dodecatriene, 3-methyl-1-butene, 1-phenylbutene-2,7,7-diethyl-1,3,5-decatriene, 1,3,5,7,9-octadecapentaene, 1,3-eicosadiene, 4-octene, 3-eicosene and 3-heptene, and the like, and mixtures thereof.

Some specific examples of cyclic olefins suitable for the reactions of this invention are cyclobutene, cyclopentene, cyclohexene, 3-methylcyclopentene, 4-ethylcyclohexene, 4-benzylcyclohexene, cyclooctene, 5-n-propylcyclooctene, cyclodecene, cyclododecene, 3,3,5,5-tetramethylcyclononene, 3,4,5,6,7-pentaethylcyclodecene, 1,5-cyclooctadiene, 1,5,9-cyclododecatriene, 1,4,7,10-cyclododecatetraene, 2-methyl-6-ethylcyclooctadiene-1,4, and the like, and mixtures thereof.

The catalysts which are useful for the present invention are those which have activity for the disproportionation of propylene into ethylene and butenes. Some examples of such catalysts are 1. silica or thoria promoted by an oxide or a compound convertible to the oxide by calcination or sulfide of tungsten or molybdenum or by an oxide or a compound convertible to the oxide by calcination of rhenium or tellurium;

2. alumina promoted with an oxide or compound convertible to an oxide by calcination of molybdenum, tungsten, or rhenium; a sulfide of tungsten or molybdenum; or an alkali metal salt, ammonium salt, alkaline earth metal salt, or bismuth salt of phosphomolybdic acid;

3. one or more of the group aluminum phosphate, zirconium phosphate, calcium phosphate, magnesium phosphate, or titanium phosphate promoted by one or more of a sulfide of molybdenum or tungsten, or an oxide or a compound convertible to the oxide by calcination of molybdenum, tungsten or rhenium or magnesium tungstate or beryllium phosphotungstate; and 4. silica, alumina, aluminum phosphate, zirconium phosphate, calcium phosphate, magnesium phosphate, or titanium phosphate promoted by a hexacarbonyl of molybdenum or tungsten.

The catalysts of (1) can be prepared and activated by conventional techniques such as by combining a catalyst grade silica with suitable tungsten, molybdenum, rhenium or tellurium compounds by a conventional method such as, for example, impregnation, dry mixing, or coprecipitation. Suitable tungsten and molybdenum compounds include tungsten oxide and molybdenum oxide and compounds convertible to these oxides. The supported oxides are activated by calcining in air and the supported sulfides are activated by heating in an inert atmosphere.

The catalysts of (2) can be prepared and activated by conventional techniques such as by combining catalyst grade alumina with an oxide or a compound convertible to an oxide by calcination of molybdenum, tungsten or rhenium and calcining the resulting mixture after removal of any solvent used in the impregnation. The sulfides of tungsten or molybdenum or the salts of phosphomolybdic acid can be utilized to impregnate a catalyst grade alumina by solution in a proper solvent after which the solvent is evaporated and the resulting mixture dried to prepare the catalyst.

The catalyst compositions of (3) can be prepared and activated by conventional techniques. For example, molybdenum oxide can be coprecipitated with aluminum phosphate followed by calcination in air to produce an activated catalyst. Alternatively, the support material can be impregnated with a compound of the promoter convertible to the oxide, such as ammonium tungstate, followed by calcination in air. In the preparation of a sulfide-containing catalyst, a sulfide of the promoter can be ball-milled with a support, such as zirconium phosphate, followed by heating in an inert atmosphere such as nitrogen. Magnesium tungstate and beryllium phosphotungstate can be dry mixed with titanium phosphate, for example, and activated by calcination in the air at elevated temperatures.

The catalyst compositions of (4) can be prepared and activated by impregnating a previously calcined support material such as calcium phosphate with a solution of the hexacarbonyl of the promoter in an organic solvent such as benzene, followed by drying in a vacuum or in an inert atmosphere at about 50° to 700° F.

The catalytic agent is considered to be the reaction product resulting from the admixture of the support material and the promoter material which is subjected to activation treatment.

The operating temperature for the process of this invention when using catalysts of (1) is in the range of about 400° to 1100° F. The process of this invention when using the catalysts of (2) will be operated at a temperature in the range of about 150° to 500° F. The process using the catalysts of (3) will be carried out at a temperature of about 600° to 1200° F. The process using the catalysts of (4) will be carried out at a temperature of about 0° to 600° F. In the process of the invention, pressures are not important but will be in the range of about 0 to 2,000 psig.

Other catalysts include those disclosed in Ser. No. 516,673, filed Dec. 27, 1965; U.S. Pat. Nos. 3,261,879, issued July 19, 1966; 3,395,196, issued July 30, 1968; 3,442,969, issued May 6, 1969; 3,444,262, issued May 13, 1969; and 3,418,390, issued Dec. 24, 1968.

The finished catalyst can be in the form of powder, or granules as well as in other shapes such as agglomerates, pellets, spheres, extrudates, beads, and depending upon the type of contacting technique which utilizes the catalyst.

A wide variety of isomerization catalysts can be used. Preferred catalysts are those which have little or no polymerization or cracking activity and which are active for isomerization at conditions suitable for obtaining a disproportionated product with the selected disproportionation catalyst. Some examples of suitable isomerization catalysts include supported phosphoric acid, bauxite, alumina supported cobalt oxide or iron oxide or manganese oxide, zinc oxide, supported alkali metal, and the like. Suitable catalysts can be selected from among those available in the art, such as the double bond isomerization catalysts listed in H. N. Dunning "Review of Olefin Isomerization," Ind. & Eng. Chem., 45, 551 (March 1953). Excellent results are obtained with magnesium oxide.

When using magnesium oxide, the reaction can be accomplished at temperatures ranging from about 50° to about 1100° F., preferably about 300° to about 900° F. at any suitable pressure and at residence times or throughput rates which will effect the desired degree of isomerization.

Magnesia suitable for use in the invention can be any suitably activated material known in the art. The material normally has a surface area of at least 1 $m^2/g$. The magnesia can be naturally occurring, such as the mineral Brucite, or can be synthetically prepared by suitable techniques. Minor amounts of other materials such as silica, alumina, and the like, can be present, but the material is principally magnesium oxide. Depending upon the contacting technique used for the isomerization, the activated magnesia can be in the form of pellets, extrudates, agglomerates, or even a fine powder. Before use in the process, the magnesium oxide is activated in a suitable manner such as by heating in a flowing stream of an oxygen-containing gas for about 1 to about 30 hours at 500° to about 1500° F., preferably 600° to about 1000° F. After activation sometimes it is advisable to flush the catalyst with an inert gas to remove any adsorbed oxygen or other gases from the magnesium oxide. The regeneration of spent magnesium oxide isomerization catalyst is generally accomplished by a technique which is similar to the activation of this material.

When preparing a mixed bed of magnesium oxide and the olefin reaction catalyst, particles of magnesium oxide and particles of the olefin reaction catalyst of about the same particle size can be blended. Alternatively, both magnesium oxide and the disproportionation catalyst can be intimately blended such as by grinding and the powder then formed into other shapes such as pellets, tablets, agglomerates, extrudates, and the like, such that each particle in the catalytic zone comprises an intimate blend of the two catalysts.

Other appropriate techniques for obtaining a composite catalyst can be used.

The proportion of magnesium oxide to the disproportionation catalyst in the composite catalyst system can vary widely. At least about 0.1 part by weight of magnesium oxide should be present for each part of weight of disproportionation catalyst and there is no theoretical upper limit for the amount of magnesium oxide which can be present. Preferred ratios, however, are 0.5 to about 20 parts by weight of magnesium oxide per part by weight of disproportionation catalyst. Equal parts of each catalyst give excellent results.

The conversion can be carried out at any convenient pressure up to about 2000 psig or higher, preferably 0 to 500 psig, and at weight hourly space velocities (WHSV) of about 0.1 to about 1000 w/w/hr. The mixed bed process can utilize any suitable contacting technique such as fixed bed reactors, fluidized bed reactors, suspended catalyst systems, and the like, and is effective with both gase phase and liquid phase operation. For example, for the conversion of normally liquid olefins, it is sometimes convenient to utilize a refluxing technique wherein the olefin charge is heated to boiling in a vessel on top of which is mounted a column containing the desired catalyst combination. The olefin vapors contact the catalyst and are converted to heavier olefins which are returned to accummulate in the vessel and to lighter olefins which rise to the top of the column. A condenser is used to return any unconverted olefin to the catalyst zone as a reflux while allowing the lighter product olefins to escape.

When using a metallic alkali metal treated olefin disproportionation catalyst, a first step in the catalyst preparation comprises associating molybdenum oxide or tungsten oxide or a molybdenum or tungsten compound convertible to the oxide upon calcination with a support such as alumina, silica, or silica-alumina. This first step can be carried out by any suitable means for the preparation of catalysts such as by impregnation, to obtain a composition containing from about 0.1 to about 30, preferably 3 to 15, weight percent of molybdenum oxide or tungsten oxide based upon the total catalytic composition. Minor amounts of other materials which are compatible with the olefin reaction can also be present in the catalyst. Some of these are titania, magnesia, cobalt oxide, and small amounts of inorganic bases such as NaOH, KOH, and the like. Some compositions particularly applicable for use in this invention comprise alumina impregnated with a molybdenum compound and with a small amount of KOH. Such a component is then activated by heating in a stream of air or other oxygen-containing gas for 0.1 to 30 hours at 700° to 1500° F., preferably 900° to 1100° F. After such an activation, the oxide composite is flushed with an inert gas such as nitrogen and maintained at such an atmosphere throughout the rest of the preparation until the finished catalyst is utilized in the reaction.

The activated oxide composite is contacted with metallic alkali metal in an amount which ranges from about 0.1 to about 30, preferably 2 to about 10, weight percent based on the total weight of the finished catalyst. In the case of catalysts having a base predominantly silica, the amount of alkali metal preferably is about 0.1 to about 5 weight percent. The contact can be carried out by any suitable means such as by contacting the solid oxide composite with either molten or vaporized alkali metal, such as sodium, for a period of time which may vary from about 1 minute to about 10 hours. This can be accomplished using sodium, for example, by melting sodium and dropping the molten sodium on a molybdena-alumina catalyst or by passing a stream of inert gas such as nitrogen or argon through the molten sodium and then over a bed of the molybdena-alumina. Contact of an alkali metal with the oxide composite generally is exothermic and causes the catalyst to take on a gray to black color.

The alkali metals utilizable in the process as selected from the group consisting of lithium, sodium, potassium, rubidium, cesium and mixtures thereof. Sodium and potassium are preferred in many instances with sodium being especially desirable.

In some instances, it has been found that pretreatment of the olefin feed with activated magnesia at relatively low temperature is unexpectedly effective in improving the ease and efficiency of the subsequent olefin reaction.

The purity of a feed is an important factor in any chemical process in that it effects directly the efficiency of even operability of that process. Olefin disproportionation processes in general require the substantial absence of materials which cause difficulty as, for example, by poisoning of the catalyst. Some of these impurities, for example, oxygen and water, are known; others are unknown. Activated magnesia is greatly superior to many other absorption agents in the purification of feed streams for the olefin reaction. Any suitably activated magnesia can be used for the pretreatment. For example, the magnesia as described above for use in the combination catalyst can be used. The benefits of the pretreatment can be obtained by contacting the feed with magnesium oxide at relatively low temperatures which may be as low as the freezing point of the olefin being treated and may be as high as a point where significant isomerization activity is observed. Frequently, ambient temperatures such as room temperatures are satisfactory for an adequate pretreatment.

Any conventional contacting device can be used for the pretreatment. For example, the olefin can be treated by passing through a fixed or fluidized bed of activated magnesia or contact can be made by suspending the magnesia, by suitable agitation in the vessel containing the olefin to be treated. The contact with the magnesia can be either in vapor or liquid phase depending upon the nature of the olefin to be treated. The time of contact, throughput rate in regard to a fixed bed of magnesia, or magnesia usage per unit weight olefin, varies greatly with the olefin being treated and the degree of treatment which may be required to bring the olefin into condition for reaction. Because the nature of the impurities removed are not always known, the optimum extent of treatment often can best be determined by trial and error.

Such an olefin pretreatment with magnesia at relatively low temperatures is advantageous even though magnesia may be present at a point downstream of the process, for example, where its isomerization activity is being exploited at somewhat higher temperatures.

Often in its use as an olefin treating agent, magnesium oxide slowly becomes discolored and deactivated. It can be regenerated using techniques similar to those of its original activation.

Where desirable, magnesium oxide can be used in conjunction with other known adsorptive materials in the pretreatment step. For example, magnesium oxide can be used either consecutively or in mixture with alumina, silica gel, molecular sieve type materials, adsorptive clays, and the like. When used in mixture, the regeneration procedure should be selected to be compatible with all components of the treating mixture. In some instances, different regeneration techniques can be used, for example, treatment with polar solvents or by first segregating mechanically and isolating any temperature sensitive component for separate treatment.

As indicated above, the specific reasons why olefin pretreatment with magnesia is extremely beneficial in some instances is not known with certainty. However, it is believed that the olefin reaction process may be sensitive to such contaminants as peroxides and hydroperoxide compounds in very low concentration and that magnesia is particularly effective in the removal of these and other impurities from olefins.

In one important embodiment of our invention, cyclic monoolefins are converted to other cyclic monoolefins having a smaller ring size by contact with the catalyst system in the presence of substantial quantities of ethylene. For example, cyclohexenes can be converted to cyclopentenes in substantial yields by contact with a catalyst system comprising magnesium oxide and silica supported tungsten oxide. The cyclic monoolefins suitable for conversion in this manner are those which contain from 6 to about 30 carbon atoms. The cyclic compounds can be substituted with one or more alkyl groups having about 5 carbon atoms. However, when such substituents are present, the double bond must be isomerizable, that is, it must be able to be shifted at least one position. Excellent results are obtained with cyclic olefins containing up to about 20 carbon atoms per molecule and especially with unsubstituted monoolefins having from about 6 to about 12 carbon atoms. The proportion of ethylene to cyclic monoolefins introduced into the reaction zone generally is in the range of about 2 to about 30 moles of ethylene per mole of cyclic olefin but even greater quantities of ethylene can be utilized, limited only by the ability to separate and recycle the unconverted ethylene conveniently. Generally, ethylene will be present in the reactor effluent. The products which are obtained by this process are cyclic monoolefins having at least one less carbon atom in the ring than in the original starting material. Propylene generally is the major by-product. To insure high yields of such cyclic products, as opposed to larger amounts of lower molecular weight acyclic products, the operating conditions will include a combination of the shortest reaction times, the lowest temperatures, and the highest pressures compatible with the specific catalyst utilized and conversion of the specific cyclic olefins being converted. The effluent of the reaction can be treated conventionally and desired products can be separated by any convenient means, such as by fractional distillation. Unconverted ethylene, as well as other olefinic products, not in the desired molecular weight range, can be recycled where appropriate.

In another important embodiment of this invention, acyclic polyenes or cyclic mono- or polyenes, having up to 30 carbon atoms per molecule, can be converted to conjugated dienes by contact with a catalyst system of the invention in the presence of substantial quantities of ethylene. When the applicable olefinic materials are converted according to this process, the products obtained, depending upon the feed materials, are 1,3-butadiene, 2-methyl-1,3-butadiene (isoprene), 2,3-dimethyl-1,3-butadiene, isobutene and propylene. These products are the fundamental products of this reaction which are not converted to lower molecular weight products. Thus, with suitable recycle and separation techniques, the applicable olefinic materials can be exhaustively reduced to one or more of the fundamental products. Unbranched starting olefinic materials can produce 1,3-butadiene while branched olefinic starting materials can produce methyl substituted butadiene. Olefinic materials applicable for use in the present invention are olefins having from 5 to about 30 carbon atoms per molecule including isomerizable acyclic polyenes and isomerizable cyclic mono- or polyenes. The olefinic materials can be branched or unbranched but the presence of one or more quaternary carbon atoms will, barring skeletal isomerization, reduce the yields of conjugated dienes. The polyolefinic materials can contain from about 2 to about 5 double bonds per molecule and can be either conjugated or nonconjugated. The proportion of ethylene to olefinic feedstocks introduced into the reaction zone will generally range from about 2 to about 30 moles of ethylene per mole of olefinic feedstock but even greater quantities of ethylene can be utilized, limited only by the ability of conveniently separate and recycle the unconverted ethylene. Generally ethylene should be present in the reactor effluent. When the cyclic olefinic materials are used as feedstocks, preferably the conversion is carried out at relatively high temperatures, at relatively low reaction pressures, and at relatively low space velocities. Thus, increased conversion of such cyclic olefinic materials to conjugated dienes is obtained at reaction temperatures which are preferably above 700° F., at reaction pressures which are generally lower than about 500 psig, and at weight hourly space velocities which are generally lower than about 25 w/w/hr., or at other combinations of these conditions which give equivalent results.

In another important embodiment of this invention, acyclic monoolefins having up to about 30 carbon atoms are converted to propylene and isobutene by contact with a catalyst system of this invention in the presence of substantial quantities of ethylene. The proportion of ethylene to cyclic monoolefins introduced into the reaction zone generally is in the range of about 2 to about 30 moles of ethylene per mole of cyclic olefin but even greater quantities of ethylene can be utilized, limited only by the ability to separate and recycle the unconverted ethylene conveniently. When the conversion is carried out according to this process, it is possible to reduce any olefin or mixture of olefins to the fundamental products of the reaction, that is, to the products which can be reduced in molecular weight no further. These fundamental products are generally propylene or isobutene but can be in some instances neohexene or substituted neohexene where the substituent is not on the vinyl group. This process finds particular utility in the removal of olefins from refinery streams from which olefins are not ordinarily separable. The conversion of olefin-containing refinery streams results in the degradation of the higher molecular weight olefins to products such as propylene and isobutene which are readily separable by distillation. Gasoline streams from which the olefins have been removed in this manner have increased value in that they are less objectionable from the standpoint of motor vehicle hydrocarbon emissions. As a further advantage, propylene and isobutene which are removed from the gasoline stream can be converted to high octane values alkylates which can be returned to the gasoline to significantly increase the octane value of the gasoline. Acyclic monoolefins which can be converted according to this process are those isomerizable olefins having from about 4 to about 30 carbon atoms per molecule. They can be branched or unbranched but the presence of one or more quaternary carbon atoms in the molecule will, barring skeletal isomerization, reduce the reactivity of the olefin. The compound 2,4,4,-trimethylpentene-2 is readily convertible to isobutene but this is generally the result of strong inclination to crack at elevated temperatures. The proportion of ethylene to the acyclic monoolefins generally is at least 2:1 but there is no theoretical upper limit. However, practical limits, determined by considerations of separation and recycle generally will be about 20:1. When it is desired to completely convert large molecules, greater quantities of ethylene are required such that an excess of ethylene is always present in the effluent.

The invention is further illustrated by the following examples:

EXAMPLE I

Pentene-2 was disproportionated in two runs. The conversion was carried out continuously by passing the pentene-2 through a stainless steel reactor tube which contained the catalyst maintained at 700° F. In one run, the catalyst bed consisted of 3.2 parts by weight of 30–50 mesh particles of a tungsten oxide on silica catalyst which had been air-activated and then given a post-activation treatment with CO at 1000° F. for 45 minutes at atmospheric pressure. In the second run, the catalyst charge consisted of a blend of 2.7 parts by weight of the above-described tungsten oxide an silica catalyst and 2.75 parts by weight of 30–50 mesh particles of magnesium oxide. The essential data and the results of these runs, in terms of the effluent analysis, are shown in the following table.

TABLE I

FIXED BED DISPROPORTIONATION OF PENTENE-2 AT 700° F.

|  | With MgO | | Without MgO | |
|---|---|---|---|---|
| Pressure; psig | 100 | 200 | 100 | 200 |
| Rate, g feed/g WO$_3$ cat/hr | 49 | 51 | 50 | 52 |
| Effluent analysis, wt. % | | | | |
| C$_2$= | 0.06 | 0.60 | 0.00 | 0.00 |
| C$_3$= | 2.37 | 2.47 | 1.00 | 0.68 |
| C$_4$= | 11.18 | 12.17 | 7.64 | 9.10 |
| C$_5$= | 71.60 | 66.10 | 82.10 | 78.60 |
| C$_6$= | 10.51 | 11.90 | 7.97 | 9.64 |
| C$_7$= | 3.86 | 4.82 | 1.16 | 1.93 |
| C$_8$= | 0.36 | 0.92 | 0.00 | 0.00 |

TABLE I-continued

FIXED BED DISPROPORTIONATION OF PENTENE-2 AT 700° F.

|  | With MgO | | Without MgO | |
|---|---|---|---|---|
| Conversion, % | 28.4 | 33.90 | 17.90 | 21.40 |

The data clearly show that under comparable conditions, the catalyst system containing the magnesium oxide resulted in a greater conversion of pentenes and a broader distribution of olefin products.

EXAMPLE II

Pentene-1 containing an unknown contaminant or contaminant detrimental to disproportionation was disproportionated in a run demonstrating the effectiveness of magnesium oxide pretreatment at relatively low temperatures and improving the conversion level. The run was carried out using a commercial pentene-1 having a purity greater than 99.0 percent in a continuous reactor at 100 psig and 537 WHSV by passing the feed substantially through a bed consisting of 10 parts by weight of granular magnesium oxide and a bed consisting of a mixture of 14 parts by weight of granular magnesium oxide and 2 parts by weight of granular tungsten oxide supported on silica. These adjacent beds were maintained at 775° F. during the run. During the initial part of the run, the feed was pretreated by passing through a bed consisting of 50 parts by weight of granular magnesium oxide preceded by 10 parts by weight of granular silica gel at ambient temperatures. During the latter part of the run, the pretreatment was omitted. The results are set forth in Table II below.

TABLE II

| Time on stream (minutes) | Conversion (percent) |
|---|---|
| 5 | 73.5 |
| 12 | 71.9 |
| 19 | 72.5 |
| 26 | 72.5 |
| 33 | 71.2 |

At this point, the pretreatment was discontinued.

| 38 | 75.4 |
| 44 | 67.8 |
| 53 | 16.1 |
| 63 | 0.5 |
| 75 | 0.4 |

EXAMPLE III

In this run, cyclohexene and ethylene were continuously converted in a fixed bed reactor. The tubular steel reactor contained, as the catalytic bed, a mixture of 5 parts by weight of a silica-supported tungsten oxide catalyst (−20 + 65 mesh) and 12 parts by weight of a magnesium oxide catalyst (−20 + 50 mesh). This intimately mixed catalyst was charged into the center of the reactor with steel packing both above and below it. The catalyst bed was activated by heating to 1000° F. in the presence of flowing air for three hours. After the air treatment, carbon monoxide was then passed over the catalyst for 10–15 minutes and the reactor was cooled at 700° F. under a carbon monoxide atmosphere.

A mixture of ethylene and cyclohexene was then passed through the reactor at 700° F., 400 psig, and at a weight hourly space velocity of 13.5 w/w/hr., based upon the cyclohexene. The molar ratio of ethylene to cyclohexene was 7.6.

After being on stream for one hour, the effluent reactor was analyzed. The analysis showed that the conversion of reactants was about 29.8 percent with about 45.6 weight percent of the products being propylene, 19.9 weight percent being cyclopentene, 10.6 weight percent being butadiene, and small amounts of other hydrocarbons, principally mono- and diolefins, making up the remainder.

EXAMPLE IV

The run of Example III was repeated under essentially the same conditions except that the reaction pressure was 750 psig.

The feed stream for the reactor consisted of an 8.7 mole ratio of ethylene to cyclohexene (which had previously been percolated through a bed of silica gel and magnesia at room temperature). The conversion was carried out at 700° F., 750 psig, and at a weight hourly space velocity of 11.8 w/w/hr.

After being on stream for about 1 hour, the effluent from the reactor was analyzed. The analysis indicated a 35.3 percent conversion of cyclohexene with 55.0 weight percent of the products being propylene, 18.8 weight percent being cyclopentene, 12.4 weight percent being butadiene, about 2.6 weight percent believed to be 1,7-octadiene, and small amounts of other hydrocarbon products making up the remainder.

These runs illustrate that the process of the present invention is capable of converting cyclohexene to substantial amounts of cyclopentene and propylene.

EXAMPLE V

Ethylene and cyclopentene were continuously converted in a fixed bed reaction. The tubular steel reactor contained, as the catalytic bed, a mixture of 5 parts by weight of a silica/tungsten oxide catalyst ($-20 + 65$ mesh) and 12 parts by weight of a magnesia catalyst ($-20 + 35$ mesh). This intimately mixed catalyst was charged into the center of the reactor with steel packing both above and below it. The catalyst bed was activated by heating the reactor and catalyst bed to 1000° F. in the presence of flowing air for 3 hours. After the air treatment, carbon monoxide was passed over the catalyst for 10 minutes and the reactor was cooled at 700° F. under a carbon monoxide atmosphere.

The feed stream consisted of ethylene and cyclopentene (which had previously been percolated at room temperature through a silica gel and magnesia bed) having a mole ratio of 7.3. The conversion was carried out at 700° F., 400 psig, and at a weight hourly space velocity of 11.7 w/w/hr (based on the cyclopentene).

After being onstream for about one hour, the effluent from the reactor was analyzed. The analysis showed that about 30 percent of the reactants were converted, with about 50 weight percent of the products being propylene, about 25 weight percent of the products being butadiene, about 8.6 weight percent believed to be 1,6-heptadiene, and several other products believed to be butene-2, butene-1, and isobutylene.

These data show that cyclopentene can be effectively converted to butadiene and propylene in high ultimate yields by using the process of the present invention.

EXAMPLE VI

A tubular steel reactor was charged with a mixture of 3 parts by weight of silica/tungsten oxide catalyst ($-20 + 50$ mesh) and 12 parts by weight magnesia ($-20 + 50$ mesh) to form a catalytic bed. Steel packing was also charged into the reactor both below and above the bed. The catalyst bed was then activated by heating the reactor and bed at 1000° F. in flowing air for 3 hours followed by contact with flowing carbon monoxide for 10 minutes. The reactor was then cooled at 700° F. under a carbon monoxide atmosphere.

The feedstock for this run was a cat-cracked gasoline (800 parts by volume) which had been fractionated to remove the light ends boiling below 75° C. (200 parts by volume) and to leave behind the heavy ends boiling above 265° C. (75 ml). This gasoline fraction was percolated through a bed of silica gel and magnesia at room temperature and then passed through the reactor together with sufficient ethylene to provide a 11.1 mole ratio of ethylene to the gasoline (having an estimated average molecular weight of about 126). The conversion was carried out at 400 psig, 700° F., and at a weight hourly space velocity of 16.2 w/w/hr. based on the gasoline.

After being on stream for about 45 minutes, the effluent from the reactor was analyzed. The analysis indicated that about 20 percent of the gasoline fraction was converted. The major olefinic products obtained were propylene in an amount of 45.5 weight percent, and isobutene in an amount of 38.6 weight percent. Other $C_4$ and $C_5$ olefinic products were also observed. The analysis indicated that essentially all of the olefins originally present in the gasoline fraction were converted. Comparable runs carried out thermally or with only magnesium oxide present gave only traces of the products obtained in the above run. This illustrates that a combination of the magnesium oxide and the silica/tungsten oxide improves the results obtained.

The data above show that the present invention can very effectively remove olefins from complex refinery streams by converting olefinic materials to other olefins such as propylene or isobutene which are easily separable from the refinery stream.

EXAMPLE VII

397 Parts by weight of a commercial molybdena-alumina (in the form of ⅛ inch pellets containing about 12.45 weight percent molybdena) were contacted with about 42 parts by weight of KOH solution (containing 0.0577 g KOH/ml) diluted with about 540 parts by weight of distilled water. The mixture was agitated and allowed to stand. The aqueous phase was tested and found to be netural to litmus paper after 25 minutes. After 2.25 hours the aqueous phase was decanted and the pellets dried by heating by a water bath under vacuum.

The above material was activated at 990° F. under a stream of air for 3 hours. The catalyst was flushed and stored under nitrogen until further use. 28.5 parts by weight of the above oxide composite was flushed with nitrogen and kept under a nitrogen atmosphere. 2 parts by weight of sodium metal was placed in the same vessel with the oxide composite and heated. At about 208° F. the sodium melted and combined with the pellets turning them black. The supply of heat was removed and the temperature increased exothermically to about 280° to 300° F. No free sodium metal was visible.

15.2 Parts by weight of the above prepared sodium-treated molybdena-alumina catalyst was charged to a nitrogen flushed tube. 21.6 Parts by weight of octene-4 was placed in a vessel and the tube mounted on the top thereof. The vessel was heated and the octene-4 was refluxed over the catalyst at ambient pressure. The refluxing and reaction were allowed to proceed for 82 minutes during which the temperature in the vessel increased to 347° F. The contents of the vessel were then sampled and analyzed by gas-liquid chromatography. The results of the analysis are shown in Table III.

For purposes of comparison, a similar conversion of octene-4 was carried out with the exception that the catalyst consisted of a molybdena-alumina which had been treated with 0.5 weight percent KOH but had not been treated with metallic sodium. After 177 minutes, the temperature in the vessel had reached only 275° F. The contents of the reactor were sampled and similarly analyzed and also appear in Table III.

TABLE III

| Catalyst Pot Temp., °C., reached in min. | $Al_2O_3$-$MoO_3$ (0.5 wt. % KOH) 130.5° C./177 min. | | Na (6.5 wt. %)-$Al_2O_3$-$MoO_3$ (0.7 wt. % KOH) 175° C./82 min. | |
| --- | --- | --- | --- | --- |
| | Wt. % | Mol. % | Wt. % | Mol. % |
| $C_3=$ | — | | 0.07 | 0.22 |
| $C_4=$ | 0.19 | 0.40 | 1.01 | 2.36 |
| $C_5=$ | 0.69 | 1.15 | 3.22 | 6.00 |
| $C_6=$ | 2.28 | 3.16 | 5.97 | 9.28 |
| $C_7$ | 9.40 | 11.15 | 5.04 | 6.71 |
| $C_8=$ | 43.40 | 45.10 | 7.58 | 8.82 |
| $C_9$ | 28.60 | 26.40 | 11.70 | 12.11 |
| $C_{10}=$ | 12.08 | 10.03 | 20.35 | 18.98 |
| $C_{11}=$ | 2.90 | 2.19 | 20.15 | 17.09 |
| $C_{12}=$ | 0.45 | 0.31 | 14.71 | 11.43 |
| $C_{13}=$ | — | — | 6.49 | 4.65 |
| $C_{14}=$ | — | — | 2.59 | 1.72 |
| $C_{15}=$ | — | — | 1.16 | 0.71 |

The data in Table III clearly show that the conversion of octene-4 over the sodium-treated catalyst resulted in a much greater conversion in a shorter length of time. The greater conversion is indicated by the smaller quantity of octenes present in the reaction vessel at the completion of the test, the greater number of olefin reaction products, and greater quantities of olefin reaction products.

Reasonable variation and modification are possible within the scope of the invention which sets forth a method for the olefin reaction.

What is claimed is:

1. A composition active for converting an olefin to obtain the product of the olefin reaction which, as defined herein, can be visualized as comprising the reaction between two first pairs of carbon atoms, the two carbon atoms of each first pair being connected by an olefinic double bond, to form two new pairs from the carbon atoms of said first pairs, the two carbon atoms of each of said new pairs being connected by an olefinic double bond comprising magnesium oxide admixed with a separate disproportionation catalyst selected from the group consisting of
    1. one or more of the group aluminum phosphate, zirconium phosphate, calcium phosphate, magnesium phosphate or titanium phosphate promoted by one or more of a sulfide of molybdenum or tungsten, or an oxide or compound convertible to the oxide by calcination of molybdenum, tungsten or rhenium, or magnesium tungstate or beryllium phosphotungstate; and
    2. silica, alumina, aluminum phosphate, zirconium phosphate, calcium phosphate, magnesium phosphate, or titanium phosphate promoted by hexacarbonyl of molybdenum or tungsten;

said magnesium oxide being present in an amount in the range of 0.1 to 20 parts by weight per part by weight of said disproportionation catalyst.

2. The composition of claim 1 wherein said disproportionation catalyst comprises an oxide of molybdenum, tungsten or rhenium on aluminum phosphate.

3. The composition of claim 1 wherein said magnesium oxide is present in an amount in the range of 0.5 to 20 parts by weight per part by weight of said disproportionation catalyst.

4. The composition of claim 3 wherein said disproportionation catalyst comprises an oxide of molybdenum, tungsten or rhenium or aluminum phosphate.

5. The composition of claim 1 wherein said disproportionation catalyst is selected from the group consisting of one or more of the group aluminum phosphate, zirconium phosphate, calcium phosphate, magnesium phosphate or titanium phosphate promoted by one or more of a sulfide or molybdenum or tungsten, or an oxide or compound convertible to the oxide by calcination of molybdenum, tungsten or rhenium, or magnesium tungstate or beryllium phosphotungstate.

6. The composition of claim 1 wherein said disproportionation catalyst is selected from the group consisting of silica, alumina, aluminum phosphate, zirconium phosphate, calcium phosphate, magnesium phosphate, or titanium phosphate promoted by hexacarbonyl of molybdenum or tungsten.

7. The composition of claim 3 wherein said disproportionation catalyst is selected from the group consisting of one or more of the group aluminum phosphate, zirconium phosphate, calcium phosphate, magnesium phosphate or titanium phosphate promoted by one or more of a sulfide or molybdenum or tungsten, or an oxide or compound convertible to the oxide by calcination of molybdenum, tungsten or rhenium, or magnesium tungstate or beryllium phosphotungstate.

8. The composition of claim 3 wherein said disproportionation catalyst is selected from the group consisting of silica, alumina, aluminum phosphate, zirconium phosphate, calcium phosphate, magnesium phosphate, or titanium phosphate promoted by hexacarbonyl or molybdenum or tungsten.

* * * * *